United States Patent
Kazlauskas et al.

(10) Patent No.: US 8,722,015 B2
(45) Date of Patent: May 13, 2014

(54) COMPOSITIONS AND METHODS FOR TREATMENT OF ANGIOGENESIS-ASSOCIATED OCULAR DISORDERS

(75) Inventors: Andrius Kazlauskas, Winchester, MA (US); Magdalena Staniszewska, Norwood, MA (US); Carmelo Romano, Benbrook, TX (US); Robert Landers, Arlington, TX (US); David P. Bingaman, Weatherford, TX (US)

(73) Assignee: The Schepens Eye Research Institute, Inc., Boston, MA (US)

( * ) Notice: Subject to any disclaimer, the term of this patent is extended or adjusted under 35 U.S.C. 154(b) by 0 days.

(21) Appl. No.: 13/078,331

(22) Filed: Apr. 1, 2011

(65) Prior Publication Data

US 2011/0305641 A1    Dec. 15, 2011

Related U.S. Application Data

(60) Provisional application No. 61/320,127, filed on Apr. 1, 2010.

(51) Int. Cl.
*A61K 49/00* (2006.01)
*A61K 38/00* (2006.01)
*A61B 5/00* (2006.01)

(52) U.S. Cl.
USPC ............... 424/9.1; 424/9.6; 514/1.1; 514/1.2; 514/1.3

(58) Field of Classification Search
None
See application file for complete search history.

(56) References Cited

U.S. PATENT DOCUMENTS

| | | | |
|---|---|---|---|
| 7,989,426 B2 * | 8/2011 | Campochiaro et al. | 514/44 R |
| 8,258,111 B2 * | 9/2012 | Shen et al. | 514/44 A |
| 8,282,921 B2 * | 10/2012 | Glidden | 424/94.61 |
| 2006/0024287 A1 * | 2/2006 | Glidden | 424/94.61 |
| 2006/0024288 A1 * | 2/2006 | Glidden | 424/94.61 |
| 2010/0003230 A1 * | 1/2010 | Glidden | 424/94.1 |
| 2010/0233194 A1 * | 9/2010 | Combal et al. | 424/184.1 |

OTHER PUBLICATIONS

Scullica et al. Documenta Ophthal. 2001. 102: 237-250.*
Chapple et al. Trends in Mol. Med. 2001. 7: 414-421.*
Burgess et al. J of Cell Bio. 1990, 111:2129-2138.*
Bowie et al. Science, 1990, 247:1306-1310.*
Pawson et al. 2003, Science 300:445-452.*
Haddad et al., Sury Ophthalmol. Jul.-Aug. 2006; 51:316-63.*
Jha et al., Mol. Immunol. Sep. 2007; 44: 3901-8.*
Landenranta et al., FASEB J. 2007, 21: 3272-32-78.*
Liu et al. Neurobiology of Disease 2005, 19: 407-418.*
Burritt et al. "Filamentous Phage Display of Olfgopeptide Libraries," *Anal. Biochem.* 238.1(1996): 1-13.
Gariano et al. "Retinal Angiogenesis in Development and Disease." *Nature.* 438.7070(2005): 960-966.
Hajitou et al. "Vascular Targeting: Recent Advances and Therapeutic Perspectives." *Trends Cardiovasc. Med.* 16.3(2006): 80-88.
Nowak. "Age-Related Macular Degneration (AMD): Pathogenesis and Therapy." *Pharmaco. Rep.* 58.3(2006): 353-363.
Rajotte et al. "Molecular Heterogeneity of the Vascular Endothellum Revelaed by In Vivo Phage Display." *J. Clin. Invest.* 102.2(1998): 430-437.
Risau "Differentiation of Endothellum." *FASEB J.* 9.10(1995): 926-933.
Witmer et al. "Vascular Endothellal Growth Factors and Angiogenesis in Eye Disease." *Prog. Retin. Eye Res.* 22.1(2003): 1-29.
Zhang et al. "Ocular Neovascularization: Implication of Endogenous Angiogenic Inhibitors and Potential Therapy." *Prog. Retin. Eye Res.* 26.1(2007): 1-37.

* cited by examiner

*Primary Examiner* — Chang-Yu Wang
(74) *Attorney, Agent, or Firm* — Mintz Levin Cohn Ferris Glovsky and Popeo, P.C.; Ingrid A. Beattie

(57) ABSTRACT

The invention provides methods and compositions for identifying and quantifying pathological changes on the retina.

6 Claims, 8 Drawing Sheets

Figure 3.

| 1 | | 2 | | 3 | |
|---|---|---|---|---|---|
| HSNYNPR | (SEQ ID NO: 4) | STEALRH | (SEQ ID NO: 2) | STEALRH | (SEQ ID NO: 2) |
| HYHEQLR | (SEQ ID NO: 5) | STEALRH | (SEQ ID NO: 2) | STEALRH | (SEQ ID NO: 2) |
| KSMEADT | (SEQ ID NO: 6) | STEALRH | (SEQ ID NO: 2) | STEALRH | (SEQ ID NO: 2) |
| QKQPHSV | (SEQ ID NO: 7) | STEALRH | (SEQ ID NO: 2) | STEALRH | (SEQ ID NO: 2) |
| QKQDSTW | (SEQ ID NO: 8) | STEALRH | (SEQ ID NO: 2) | STEALRH | (SEQ ID NO: 2) |
| QTMLSLN | (SEQ ID NO: 9) | STEALRH | (SEQ ID NO: 2) | STEALRH | (SEQ ID NO: 2) |
| PAQLLNA | (SEQ ID NO: 10) | SHEALRH | (SEQ ID NO: 35) | STEALRH | (SEQ ID NO: 2) |
| TVDKPPG | (SEQ ID NO: 11) | SHEALRH | (SEQ ID NO: 35) | STEALRH | (SEQ ID NO: 2) |
| QPPFPRP | (SEQ ID NO: 12) | SSEAYRH | (SEQ ID NO: 36) | STEALRH | (SEQ ID NO: 2) |
| RFNTPLP | (SEQ ID NO: 13) | NMDTARL | (SEQ ID NO: 37) | STEALRH | (SEQ ID NO: 2) |
| RHSANQT | (SEQ ID NO: 14) | STTPSRM | (SEQ ID NO: 38) | STEALRH | (SEQ ID NO: 2) |
| YQDPRQP | (SEQ ID NO: 15) | DSTTPRS | (SEQ ID NO: 39) | STEALRH | (SEQ ID NO: 2) |
| EGLSEIE | (SEQ ID NO: 16) | SQPTLQA | (SEQ ID NO: 40) | STEALRH | (SEQ ID NO: 2) |
| PQLSDAG | (SEQ ID NO: 17) | TPTTSPA | (SEQ ID NO: 41) | STEALRH | (SEQ ID NO: 2) |
| LPLRSIQ | (SEQ ID NO: 18) | MHSGPMA | (SEQ ID NO: 42) | STEALRH | (SEQ ID NO: 2) |
| LPNIDAK | (SEQ ID NO: 19) | ANLHHQQ | (SEQ ID NO: 43) | NSYTNAA | (SEQ ID NO: 60) |
| PNSRVAA | (SEQ ID NO: 20) | SEYLWST | (SEQ ID NO: 44) | DTTNSHL | (SEQ ID NO: 61) |
| RPSHATP | (SEQ ID NO: 21) | NFTWTSL | (SEQ ID NO: 45) | DTTNSHL | (SEQ ID NO: 61) |
| SAGFTWL | (SEQ ID NO: 22) | NKLEPFR | (SEQ ID NO: 46) | DTTNSHL | (SEQ ID NO: 61) |
| SLEMTWK | (SEQ ID NO: 23) | YPTHPYS | (SEQ ID NO: 47) | DTTNSHL | (SEQ ID NO: 61) |
| RSPMTTY | (SEQ ID NO: 24) | KWSPPQS | (SEQ ID NO: 48) | NQKTTSS | (SEQ ID NO: 52) |
| IESPTYW | (SEQ ID NO: 25) | MSPKNVS | (SEQ ID NO: 49) | NQKTTSS | (SEQ ID NO: 52) |
| HQSSPKL | (SEQ ID NO: 26) | PTAKSAS | (SEQ ID NO: 50) | QQPTSGH | (SEQ ID NO: 62) |
| QSSPPSL | (SEQ ID NO: 27) | LAPTANS | (SEQ ID NO: 51) | TERQTRF | (SEQ ID NO: 63) |
| LITPSRL | (SEQ ID NO: 28) | NQKTTSS | (SEQ ID NO: 52) | RDMGNHI | (SEQ ID NO: 59) |
| NPDRYYT | (SEQ ID NO: 29) | VDKSFNI | (SEQ ID NO: 53) | KTPFQHT | (SEQ ID NO: 64) |
| NSTHKMF | (SEQ ID NO: 30) | GLNVMRY | (SEQ ID NO: 54) | GLNVMRY | (SEQ ID NO: 54) |
| YLQLLLT | (SEQ ID NO: 31) | PDNKLRQ | (SEQ ID NO: 55) | | |
| PGRQAMP | (SEQ ID NO: 32) | DGQSTLR | (SEQ ID NO: 56) | | |
| TPITLST | (SEQ ID NO: 33) | HDNRSAL | (SEQ ID NO: 57) | | |
| RAYQLQQ | (SEQ ID NO: 34) | EQPYSSI | (SEQ ID NO: 58) | | |
| | | RDMGNHI | (SEQ ID NO: 59) | | |
| | | | | | |
| no consensus | | STEALRH | (SEQ ID NO: 2) | STEALRH | (SEQ ID NO: 2) |

Figure 3 (Con't).

| 4 | | 5 | |
|---|---|---|---|
| STEALRH | (SEQ ID NO: 2) | STEALRH | (SEQ ID NO: 2) |
| STEALRH | (SEQ ID NO: 2) | STEALRH | (SEQ ID NO: 2) |
| STEALRH | (SEQ ID NO: 2) | STEALRH | (SEQ ID NO: 2) |
| STEALRH | (SEQ ID NO: 2) | STEALRH | (SEQ ID NO: 2) |
| STEALRH | (SEQ ID NO: 2) | STEALRH | (SEQ ID NO: 2) |
| STEALRH | (SEQ ID NO: 2) | STEALRH | (SEQ ID NO: 2) |
| STEALRH | (SEQ ID NO: 2) | STEALRH | (SEQ ID NO: 2) |
| STEALRH | (SEQ ID NO: 2) | STEALRH | (SEQ ID NO: 2) |
| STEALRH | (SEQ ID NO: 2) | STEALRH | (SEQ ID NO: 2) |
| STEALRH | (SEQ ID NO: 2) | STEALRH | (SEQ ID NO: 2) |
| STEALRH | (SEQ ID NO: 2) | STEALRH | (SEQ ID NO: 2) |
| STEALRH | (SEQ ID NO: 2) | STEALRH | (SEQ ID NO: 2) |
| STEALRH | (SEQ ID NO: 2) | STEALRH | (SEQ ID NO: 2) |
| STEALRH | (SEQ ID NO: 2) | STEALRH | (SEQ ID NO: 2) |
| STEALRH | (SEQ ID NO: 2) | STEALRH | (SEQ ID NO: 2) |
| STEALRH | (SEQ ID NO: 2) | STEALRH | (SEQ ID NO: 2) |
| STEALRH | (SEQ ID NO: 2) | STEALRH | (SEQ ID NO: 2) |
| STEALRH | (SEQ ID NO: 2) | STEALRH | (SEQ ID NO: 2) |
| STEALRH | (SEQ ID NO: 2) | STEALRH | (SEQ ID NO: 2) |
| STEALRH | (SEQ ID NO: 2) | STEALRH | (SEQ ID NO: 2) |
| STEALRH | (SEQ ID NO: 2) | STEALRH | (SEQ ID NO: 2) |
| STEALRH | (SEQ ID NO: 2) | STEALRH | (SEQ ID NO: 2) |
| STEALRH | (SEQ ID NO: 2) | NTEALRH | (SEQ ID NO: 66) |
| STEALRH | (SEQ ID NO: 2) | NQKTTSS | (SEQ ID NO: 52) |
| STEALRH | (SEQ ID NO: 2) | TERQTRF | (SEQ ID NO: 63) |
| STEALRH | (SEQ ID NO: 2) | SEYLWST | (SEQ ID NO: 44) |
| LQMTKNS | (SEQ ID NO: 65) | KTPFQHT | (SEQ ID NO: 64) |
| LQMTKNS | (SEQ ID NO: 65) | | |
| NQKTTSS | (SEQ ID NO: 52) | | |
| TERQTRF | (SEQ ID NO: 63) | | |
| ANLHHQQ | (SEQ ID NO: 43) | | |
| SEYLWST | (SEQ ID NO: 44) | | |
| | | | |
| STEALRH | (SEQ ID NO: 2) | STEALRH | (SEQ ID NO: 2) |

COMPOSITIONS AND METHODS FOR TREATMENT OF ANGIOGENESIS-ASSOCIATED OCULAR DISORDERS

RELATED APPLICATIONS

This application claims priority to U.S. Ser. No. 61/320,127, filed on Apr. 1, 2010, which is incorporated herein by reference in its entirety.

INCORPORATION-BY-REFERENCE OF SEQUENCE LISTING

The contents of the text file named "36770-511001US_ST25.txt," which was created on Jun. 22, 2013 and is KB in size, are hereby incorporated by reference in their entirety.

FIELD OF THE INVENTION

This invention relates generally to the field of ophthalmology.

BACKGROUND OF THE INVENTION

Angiogenesis, the formation of new blood vessels from preexisting vasculature, is a major component in several retinal vascular diseases causing blindness, such as retinopathy of prematurity, proliferative diabetic retinopathy, and age-related macular degeneration. While a small subset of current approaches to measure the extent of pathological neovascularization can selectively recognize neovessels, these approaches are not able to distinguish between new vessels that are emerging because of a physiological need (i.e., physiological neovessels) from those that lead to pathology (i.e., pathological neovessels) without time consuming and labor intensive manual retinal examination. As such, there has been a long-felt need in the art for the discovery of new approaches to identify and quantify the extent of pathological changes in the retina.

SUMMARY OF THE INVENTION

The invention is based on the surprising discovery that certain amino acid sequences recognize pathological neovascular changes on the retinal surface. The invention also concerns the use of neovascular-specific motifs to diagnose and treat diseases associated with ocular angiogenesis.

The invention provides an ophthalmic composition for treating an ophthalmic condition or disorder comprising an amino acid sequence selected from the group consisting of SEQ ID NOs: 1-3, and a pharmaceutically acceptable carrier. Also provided are larger peptides and proteins that recognize and treat pathological neovascular changes on the retinal surface. Optionally, the ophthalmic condition or disorder is an angiogenic-associated disorder selected from the group consisting of retinopathy of prematurity, proliferative diabetic retinopathy, age-related macular degeneration, and central retinal vein occlusion. In one aspect, the composition is in the form of eye drops, ointment, gel, or an ocular insert.

The invention also provides methods of identifying pathological alterations on the retinal surface of a subject comprising locally administering to the retina of the subject an amino acid sequence that binds to pathological neovessels. In one aspect, the amino acid sequence is selected from the group consisting of SEQ ID NOs: 1-3. In addition to small peptides, the invention also provides that large peptides, polypeptides, and proteins are utilized to identify pathological alterations on the retinal surface. Suitable proteins include, e.g., those composed of about 20 or more amino acids linked in a genetically controlled linear sequence. For example, the peptide, polypeptide, or protein comprises at least 2 amino acids, at least 5 amino acids, at least 10 amino acids, at least 15 amino acids, at least 20 amino acids, at least 25 amino acids, at least 50 amino acids, or at least 100 amino acids, at least 200 amino acids, or at least 300 amino acids. Preferably, the amino acid sequence is fluorescently labeled. For example, a fluorescent molecule such as a derivative of rhodamine, ethidium bromide, fluorescein, green fluorescent protein (GFP), or fluorescein isothiocyanate (FITC), is linked to the N-terminus or the C-terminus of the peptide. The linkage is covalent or ionic. In one example, a terminus of the peptide comprises biotin and the bound peptide is detected by fluorescently labeled avidin.

The invention also provides methods of treating an ophthalmic condition or disorder in a subject in need thereof comprising the steps of: (a) identifying a subject with an ophthalmic condition or disorder; and (b) locally administering to the retina of the subject a fusion protein comprising an amino acid sequence that binds to pathological neovessels and an inhibitor of angiogenesis, and a pharmaceutically acceptable carrier, thereby reducing pathological neovascularization, and treating the ophthalmic condition or disorder. In one aspect, the amino acid sequence is selected from the group consisting of SEQ ID NOs: 1-3. Alternatively, larger peptides and proteins that recognize pathological neovascular changes on the retinal surface are utilized to treat ophthalmic conditions or disorders. Optionally, the ophthalmic condition or disorder is an angiogenic-associated disorder selected from the group consisting of retinopathy of prematurity, proliferative diabetic retinopathy, age-related macular degeneration, and central retinal vein occlusion. The composition is in the form of eye drops, ointment, gel, or an ocular insert. Suitable inhibitors of angiogenesis include agents that block the action of pro-angiogenic agents such as vascular endothelial growth factor (VEGF, GenBank Accession Number CAC19515 (GI:220732298), incorporated herein by reference), and anti-angiogenic agents such as angiopoietin-2 (Ang-2, GenBank Accession Number ANGP2_HUMAN, (GI:12229555), incorporated herein by reference), angiostatin (GenBank Accession Number 1KI0_A (GI:21465835), incorporated herein by reference), endostatin (GenBank Accession Number AAK50626 (GI:13957730), incorporated herein by reference), tumstatin (GenBank Accession Number AF258351_1 (GI:8101726), incorporated herein by reference), pigment epithelium-derived factor (PEDF, GenBank Accession Number AF400442_1 (GI:15217079), incorporated herein by reference, etc. For example, the inhibition of angiogenesis is linked, e.g., covalently linked or cross-linked, to the peptide of SEQ ID NO 1, 2, or 3.

The invention also provides methods of identifying a peptide that binds to pathological neovessels comprising the steps of: (a) displaying a candidate peptide or protein on the surface of a phage; and (b) determining if the candidate peptide or protein specifically binds to pathological neovessels. Additional details for these two steps are provided in Examples 1 and 2 that are located towards the end of this document.

The invention also provides an isolated peptide comprising SEQ ID NO: 1, SEQ ID NO: 2, or SEQ ID NO: 3. Also provided is a bacteriophage comprising a peptide comprising the amino acid sequence of SEQ ID NO: 1, 2, or 3.

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. The terms "preventing" and "prevention" refer to the administration of an agent or composition to a clinically asymptomatic individual who is susceptible to a particular adverse condition, disorder, or disease, and thus relates to the prevention of the occurrence of symptoms and/or their underlying cause. The subject is preferably a mammal in need of such treatment. The mammal can be, e.g., any mammal, e.g., a human, a primate, a mouse, a rat, a dog, a cat, a cow, a horse, or a pig. In a preferred embodiment, the mammal is a human.

By the terms "effective amount" and "therapeutically effective amount" of a formulation or formulation component is meant a nontoxic but sufficient amount of the formulation or component to provide clinical benefit.

Optionally, peptides, polypeptides and proteins of the invention are purified and/or isolated. A purified peptide or protein is characterize by a degree of sterility that is safe for administration to a human subject, e.g., lacking infectious or toxic agents. Specifically, as used herein, an "isolated" or "purified" peptide, polypeptide, or protein is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. Purity is measured by any appropriate standard method, for example, by column chromatography, polyacrylamide gel electrophoresis, or HPLC analysis.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, Genbank/NCBI accession numbers, and other references mentioned herein are incorporated by reference in their entirety. In the case of conflict, the present specification, including definitions, will control. In addition, the materials, methods, and examples are illustrative only and not intended to be limiting.

BRIEF DESCRIPTION OF THE DRAWINGS

FIG. 3 is a schematic demonstrating a peptide consensus sequence in an OIR-binding phage pool. The OIR-binding phage pool is enriched in phage expressing the amino acid sequence the amino acid sequence STEALRH(SH).

In FIGS. 4A and 4B, the top row was stained with the SH phage, which has a unique peptide insert sequence, whereas the bottom row was stained with the control phage that lacks a peptide insert.

FIG. 5A is a photomicrograph showing vessels stained with IB4 (identifying endothelial cells/activated macrophages/microglia) and CD11b (identifying macrophage/microglia). FIG. 5B is a photomicrograph showing vessels stained with IB4 and NG2 (identifying pericytes). FIG. 5C is a photomicrograph showing vessels stained with IB4 and glial fibrillary acidic protein (GFAP, identifying astrocytes)—the focal plane is at the level of the inner limiting membrane (ILM). FIG. 5C' is a photomicrograph showing vessels stained with IB4 and GFAP—the focal plane is below the level of the ILM.

FIG. 6A shows a photomicrograph of a healthy retina, while FIG. 6B shows a photomicrograph of a pathological retina, both of which were stained with anti-CD11b, which stains macrophages/microglia. DAPI staining is included in the enlargements in order to indicate the presence of a tuft. Bars are 50 micrometers.

DETAILED DESCRIPTION

Figure 1:
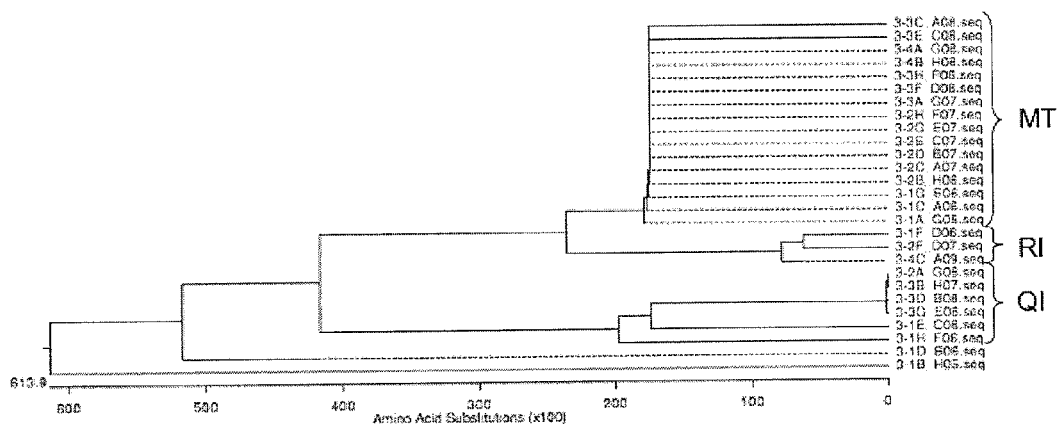
FIG. 1 is a schematic showing the phylogenetic tree of the phage present in oxygen-induced retinopathy 3 (OIR3).

The present invention provides compositions and methods for diagnosing, treating and/or preventing ophthalmic or ocular disorders, diseases or conditions, and compositions and methods for treating or preventing ophthalmic or ocular conditions and disorders in a subject in need thereof. The subject is preferably a mammal in need of such treatment. Subjects in need of treatment for ophthalmic or ocular conditions and disorders are identified using techniques well known to those skilled in the art. Specifically, diagnostic criteria are set forth in, e.g., The International Statistical Classification of Diseases and Related Health Problems (ICD) published by the World Health Organization. The mammal can be, e.g., any mammal, e.g., a human, a primate, a mouse, a rat, a dog, a cat, a cow, a horse, or a pig. In a preferred embodiment, the mammal is a human. Examples of these conditions include proliferative diabetic retinopathy, age-related macular degeneration (AMD), retinopathy of prematurity, and retinal branch vein occlusion. The terms "ophthalmic" and "ocular" are used interchangeably herein.

Retina Structure

The vertebrate retina is a light sensitive tissue lining the inner surface of the eye. The optics of the eye create an image of the visual world on the retina, which serves much the same function as the film in a camera. Light striking the retina initiates a cascade of chemical and electrical events that ultimately trigger nerve impulses. These are sent to various visual centers of the brain through the fibers of the optic nerve. A number of changes can occur in the retina with age. For example, atherosclerotic buildup and leakage in the retinal arteries can lead to macular degeneration as well as reduction of peripheral vision. Rods and cones of the retina can become less sensitive over time, as they replenish their pigments more slowly. Progressively, all these effects can reduce vision, ultimately leading to partial or complete blindness. Retinal diseases such as age-related macular degeneration are difficult to treat, and current retinal treatments include invasive laser surgery to stop the leaking of blood vessels in the eye.

Retina Pathology

Retinal diseases include proliferative diabetic retinopathy, age-related macular degeneration (AMD), retinopathy of prematurity, and retinal branch vein occlusion. A branch retinal vein occlusion refers to a blockage of the portion of the circulation that drains the retina of blood. As the arteries deliver blood to the retina, red blood cells and plasma course through the capillaries and into the venous system, eventually reaching the central retinal vein. With blockage of any vein, there is back-up pressure in the capillaries, which causes hemorrhaging and fluid leakage on the retina. Usually, such occlusions occur at sites where an artery and vein cross. The occlusion site determines the extent or distribution of the hemorrhage, ranging from small branch veins giving rise to a quadranic occlusion involving one fourth of the retina to a hemispheric (hemi-retinal) occlusion involving one half of the retina. An occlusion of the central retinal vein involves the entire retina, and is referred to as a central retinal vein occlusion.

Retinopathy of prematurity (ROP), previously known as retrolental fibroplasia (RLF), is an eye disease that affects prematurely born babies. It is thought to be caused by disorganized growth of retinal blood vessels which may result in scarring and retinal detachment. ROP can be mild and may resolve spontaneously, but may lead to blindness in serious cases. As such, all preterm babies are at risk for ROP, and very low birth weight is an additional risk factor. Both oxygen toxicity and relative hypoxia can contribute to the development of ROP.

Diabetic retinopathy (DR) remains the most common cause of vision impairment in working-age adults in the United States and Europe, and retinal neovascularization occurs in up to 20% of patients with diabetes. Pathological retinal neovascularization in patients with diabetes results from an imbalance of pro-angiogenic and anti-angiogenic factors. In addition to vascular endothelial growth factor (VEGF) accumulation in eyes with diabetic retinal neovascularization, changes in numerous other cytokines, chemokines, adhesion molecules, vasoactive hormones and immune cells have been reported. Together, these changes constitute a complex inflammatory process that results in an aberrant wound-healing response. All retinal cell types, including neurons, glial, microglial and vascular cells, are believed to be affected by diabetes, resulting in a neurovascular disorder. The retinal neurovascular degeneration of diabetes includes neuronal and vascular cell apoptosis, and microglial and glial cell activation, which provides intraretinal sources of cytokines and chemokines (Gariano & Gardner, *Nature* 438, 960-966, 2005).

Clinically, diabetic retinopathy (DR) is classified into two stages: non-proliferative DR (NPDR) and proliferative DR (PDR). In NPDR, VEGF-A (which is known to act as a survival factor for endothelial cells, via induction of anti-apoptotic proteins) expression in elevated levels has been described in human and in experimental models of DR. VEGFRs are also upregulated in NPDR. VEGF-A may be increased initially in preclinical DR as a mechanism to maintain the integrity of the retinal vascular bed. In a later stage, high VEGF-A production in ischemic areas, where VEGFR-2 is upregulated, then leads to vascular leakage and neovascularization. In proliferative DR (PDR), intra-ocular neovascularization is likely caused by high levels of VEGF-A in the vitreous derived from widespread production of this factor by ischemic retina. Elevated levels of VEGF-A have been found in the aqueous humor and vitreous of patients with PDR (Witmer et al., *Prog Ret Eye Res* 22, 1-29, 2003).

Age-Related Macular Degeneration (AMD) is one of the leading causes of irreversible vision loss in the Western world, accounting for 75% of legal blindness in the population of age 50 years old or older in the developed countries (Zhang & Ma, *Prog Ret Eye Res* 26, 1-37, 2007). Two subgroups of AMD are classically distinguished: atrophic (dry form) and exudative (wet form). The dry form (also known as geographic atrophy, both central and/or non-central) is typically characterized by a progressing course leading to degeneration of retinal pigment epithelium (RPE) and photoreceptors. The exudative form is linked to choroidal neovascularization (CNV, the abnormal growth of blood vessels that originate from the choroidal vasculature) directed to the subretinal macular region, with subsequent bleeding and/or fluid leakage, which may result in a sudden loss of central vision; it is the most rapidly progressing form of AMD. Clinical features common for the two types of AMD include the presence of drusen, which is defined as the complex deposits of lipids, proteins, and inflammatory mediators that develop in the Bruch's membrane under the RPE, as well as hypo- and/or hyperpigmentation of the RPE. More than 80% of all people with intermediate and advanced AMD have the dry form, yet this form may progress to the wet form which leads to significantly more vision loss (Zhang & Ma, *Prog Ret Eye Res* 26, 1-37, 2007; Nowak, *Pharmacol Reports* 58, 353-363, 2006).

The pathophysiology of AMD is complex and, in addition to genetic predispositions, at least four processes contribute to the disease, i.e., lipofuscinogenesis (with its linkage to oxidative stress), drusogenesis, local inflammation and neovascularization (in the case of wet form). In order to stimulate the process of angiogenesis, including CNV, the angiogenesis-linked molecular machinery must be disbalanced in a way promoting functional overactivity of pro-angiogenic signaling. This may result from either an unbalanced increase in pro-angiogenic (e.g., VEGF) activity or an unbalanced decrease in anti-angiogenic (e.g., pigment epithelium derived factor, PEDF) activity. Despite many similarities in the pathways leading to the retinal and choroidal neovascularization, there are some major differences between these two types of angiogenesis. In the initiation and development of CNV, there may be a role for local inflammation together with immune reactions as a process creating cellular and molecular milieu promoting the prevalence of pro-angiogenic mechanisms. In fact, neutrophils, macrophages, mast cells, activated microglia, all are capable of producing and releasing an array of pro-angiogenic factors, including VEGF. Recent findings confirm the role of VEGF and pigment epithelium-derived factor (PEDF) as important regulators engaged in CNV, and this fact has already its impact on establishing therapeutic strategies to combat the existing or to prevent the development of newly formed unwanted blood vessels (Nowak, *Pharmacol Reports* 58, 353-363, 2006). In patients with AMD, high levels of VEGF and VEGF receptor have been detected in the subfoveal fibrovascular membrane, the surrounding tissues and the RPE (Zhang & Ma, *Prog Ret Eye Res* 26, 1-37, 2007).

Angiogenesis, the formation of new blood vessels from preexisting vasculature, is a major component in several retinal vascular diseases causing blindness, such as retinopathy of prematurity, proliferative diabetic retinopathy, and age-related macular degeneration described above. Diabetes mellitus is the main cause of new cases of adult blindness. Nearly all individuals with type 1 diabetes show some symptoms of diabetic retinopathy, usually ~20 years after clinical recognition of diabetes; in the most advanced form of diabetic retinopathy, called proliferative diabetic retinopathy, new blood vessels grow uncontrollably on the retinal inner surface, causing hemorrhages and even retinal detachment. Surgical and laser photocoagulation treatments are only partially effective and may further damage the retinal tissue. Prior to the invention, neither pathogenetic mechanisms, nor effective therapy were available for retinopathy of prematurity, diabetic retinopathy, or age-related macular degeneration. Recent reports indicate that angiogenesis, whatever its cause, involves an increase in demonstrable markers (Landenranta, et al. 2007 FASEB J., 21:3272-3278). The use of vascular receptors or markers discovered by in vivo phage display for ligand based vascular targeting has been explored in cancer research (Hajitoou, et al. 2006 Trends Cardiovasc Med, 16:80-88). As described herein, such angiogenic markers enable the identification and quantification of pathological changes on the retina.

Accordingly, the invention is based on the surprising discovery that peptides containing specific amino acid sequences recognize pathological neovascular changes on the retinal surface. As described below, the bacteriophages that encode this sequence can distinguish between healthy retinas and those with pathology, e.g., oxygen-induced retinopathy (OIR). Moreover, the invention provides for neovascular-specific amino acid sequence motifs to diagnose and treat diseases associated with ocular angiogenesis. For example, the invention provides that small peptides, large peptides, and proteins that recognize pathological neovascular changes on the retinal surface are utilized to treat ophthalmic conditions or disorders, such as each of the conditions described above.

Prior to the invention, the existing methods to measure the extent of pathological neovascularization in the animal models of proliferative retinopathy concentrated on labeling and quantifying endothelial cells or neovascular tufts. A significant drawback of these approaches is that they typically label both quiescent vessels and neovessels. While a small subset of these approaches can selectively recognize neovessels, they are not able to distinguish between new vessels that are emerging because of a physiological need (i.e., physiological neovessels) from those that lead to pathology (i.e., pathological neovessels). The way this issue has been overcome in the past is by manually examining the retinas to assess the location and morphology of the neovessels, which allows for the recognition of both physiological and pathological neovessels. However, manual retinal examination is time consuming and labor intensive.

Current available treatment for ocular angiogenesis-related diseases such as age-related macular degeneration and diabetic retinopathy involves 1) laser photocoagulation via photodynamic therapy (VISUDYNE®, or Verteporfin) and/or surgical intervention; or 2) intravitreal injections of anti-VEGF compounds such as LUCENTIS® (ranibizumab), AVASTIN® (bevacizumab) and MACUGEN® (pegaptanib). Laser-associated treatment has side-effects associate with nonspecific damage to surrounding tissues. Although anti-VEGF treatment directly interferes with the pathologic mechanisms responsible for abnormal neovessel growth and provides relatively better outcome, it also abrogates VEGF's neuronal-protective effect. In addition, such treatment also inhibits normal physiological retinal vessel growth, which is present in children.

In previous reports, authors demonstrated that a phage harboring peptides that included an RDV motif specifically bound to endothelial cells in retina (Rajotte, et al. 1998 J. Clin. Invest, 102: 430-437). A related publication showed that phage, which encoded peptides that had an RGD motif could be used as a tool to distinguish between endothelial cells in resting and actively proliferating vessels (Landenranta et al., 2007 FASEB, 12:3272-3278). However, these phages did not differentiate between physiological and pathological neovessels. The invention provides for a phage that expresses the amino acid sequence STEALRH (SEQ ID NO: 2) on its surface (i.e., an SH phage) that specifically marked pathological retina in a rat model of OIR, but did not label the retina from a healthy animal. As described below, receptors or ligands are fused to effector molecules (e.g., radio-labeled cytotoxic agents or antiangiogenic agents), thereby enabling the homing of receptors or ligands to the target tissue. Thus, the phages described herein are tools for identification and quantification of retinal pathology related to proliferative retinopathy and other angiogenesis-associated disorders.

Phage display peptide libraries are commonly used to obtain defined peptide sequences interacting with a particular molecule (Rajotte, et al. 1998 J. Clin. Invest., 102(2):430-437). In this system, peptides are expressed on the phage surface by fusion to one of the phage surface proteins and the desired peptides are selected on the basis of binding to the target molecule (Burritt, et al. 1996 Anal. Biochem., 238:1-13). Thus, phage display technology is a powerful method enabling unbiased selection of peptides capable of homing selectively to different vascular beds in mammals, e.g., mice and humans. This method also allows tissue-specific targeting of angiogenesis-related molecules to tumor blood vessels. Peptide ligands selected through phage display technology deliver therapeutic peptides selectively, showing marked therapeutic efficacy in tumor-bearing mouse models.

The invention provides a unique peptide (CSTEALRHC; SEQ ID NO: 1) that identifies pathological retinal neovascularization in mammals such as rats. The vascular beds in different parts of body are known to be morphologically and functionally different. Studies, especially in tumor angiogenesis, demonstrate that vascular endothelium expresses differential biomarkers or receptors depending on the functional state and tissue localization (Trepel, et al. 1995 FASEB, 9(10):926-33). As described below, a random phage-display peptide library technique was used to directly select specific markers present on the surface of the pathological retina from rats subjected to oxygen-induced retinopathy. Using this technique, one specific peptide contains amino acids CSTEALRHC (SEQ ID NO: 1). This peptide is present at the N-terminus of a protein (pIII) expressed on the surface of M13KE filamentous bacteriophage (SH), and is essential for the phage to bind to the pathological retina of a rat retina with oxygen-induced retinopathy (OIR). Since the phage that expresses the amino acid sequence STEALRH (SEQ ID NO: 2) on its surface (i.e., the SH phage) and CSTEALRHC (SEQ ID NO: 1) peptide recognize the specific marker on retinal pathological neovessels, using it as a homing molecule to direct anti-angiogenic compounds provides safe and efficacious treatment for ocular angiogenesis.

The invention provides for the use of peptide CSTEALRHC (SEQ ID NO: 1) or the phage that expresses the amino acid sequence STEALRH (SEQ ID NO: 2) on its surface (i.e., the SH phage, so named due to the first and last amino acids in the peptide sequence). The specific interactions of the peptide/phage with the target molecule on the retinal surface allow identification of pathological changes on retinal surface related to proliferative retinopathy. The methods described herein enable quick, quantitative and specific measurement of pathological neovascularization (NV) formation, e.g., in the rat model of OIR, which is a widely accepted in vivo model for anti-angiogenic compound screening. The methods described herein are clinical diagnostic tools for identification of human diseases characterized by ocular angiogenesis, such as age-related macular degeneration (AMD), proliferative diabetic retinopathy (PDR), retinopathy of prematurity, or retinal branch vein occlusion. As rodent gene and protein sequences share homology with human gene and protein sequences, the compositions and methods are also useful for the identification of human proteins that bind to the pathological retina, thereby allowing for clinical diagnosis and treatment evaluation in the diseases mentioned above. Moreover, the peptides of the invention serve as vascular targeting agents to direct anti-angiogenic compounds to the precise site of pathological neovascularization and to provide safe and efficacious treatment of diseases associated with ocular angiogenesis and associated sequela within the posterior segment, e.g., retinal vascular leakage and edema. Finally, the invention provides for methods of drug discovery utilizing the specific proteins or receptors (potentially novel therapeutic targets) that interact with the unique peptides that bind to the pathological retina.

There are numerous advantages associated with the compositions and methods described herein. Prior to the invention, methods were unable to distinguish between new vessels that were emerging because of a physiological need (i.e., physiological neovessels) from those that lead to pathology (i.e., pathological neovessels) without time consuming and labor intensive manual retinal examination. The SH phage described herein recognizes more than just the neovessels, and hence is a unique tool to assess retinopathy, i.e., a tool that is not based on the endothelial cells. The SH phage distinguishes between quiescent endothelium and pathological neovessels. This difference is readily quantified. Optionally, the quantification is automated.

Administering the formulation to the eye can involve drops, injections, or implantable devices, depending on the precise nature of the formulation and the desired outcome of the administration. Specifically, a composition of the invention is delivered directly to the eye, (e.g., topical ocular drops or ointments; slow release devices such as pharmaceutical drug delivery sponges implanted in the cul-de-sac or implanted adjacent to the sclera or within the eye; and periocular, conjunctival, sub-tenons, intracameral, intravitreal, or intracanalicular injections), or systemically (e.g., orally; intravenous, subcutaneous or intramuscular injections; parenteral, dermal or nasal delivery) using techniques well known by those of ordinary skill in the art. In another example, a peptide as disclosed herein is formulated in intraocular inserts or implantable devices as dispersed throughout the insert or device (e.g., wherein the peptide diffuses out the device once administered to the eye) or as a coating on the insert or device, as described further below.

The ophthalmic formulations of the invention are administered in any form suitable for ocular drug administration, e.g., dosage forms suitable for topical administration, a solution or suspension for administration as eye drops or eye washes, ointment, gel, liposomal dispersion, colloidal microparticle suspension, or the like, or in an ocular insert, e.g., in an optionally biodegradable controlled release polymeric matrix. The ocular insert is implanted in the conjunctiva, sclera, pars plana, anterior segment, or posterior segment of the eye. Implants provide for controlled release of the formulation to the ocular surface, typically sustained release over an extended time period. Additionally, in a preferred embodiment, the formulation is entirely composed of components that are naturally occurring and/or as GRAS ("Generally Regarded as Safe") by the U.S. Food and Drug Administration.

The pharmaceutically acceptable carrier of the formulations of the invention may comprise a wide variety of non-active ingredients which are useful for formulation purposes and which do not materially affect the novel and useful properties of the invention. By a "pharmaceutically acceptable" or "ophthalmologically acceptable" component is meant a component that is not biologically or otherwise undesirable, i.e., the component may be incorporated into an ophthalmic formulation of the invention and administered topically to a patient's eye without causing any undesirable biological effects or interacting in a deleterious manner with any of the other components of the formulation composition in which it is contained. When the term "pharmaceutically acceptable" is used to refer to a component other than a pharmacologically active agent, it is means that the component has met the required standards of toxicological and manufacturing testing or that it is included on the Inactive Ingredient Guide prepared by the U.S. Food and Drug Administration.

The compositions administered according to the present invention optionally also include various other ingredients, including but not limited to surfactants, tonicity agents, buffers, preservatives, co-solvents and viscosity building agents. In carriers that are at least partially aqueous one may employ thickeners, isotonic agents, buffering agents, and preservatives, providing that any such excipients do not interact in an adverse manner with any of the formulation's other components.

Suitable thickeners will be known to those of ordinary skill in the art of ophthalmic formulation, and include, by way of example, cellulosic polymers such as methylcellulose (MC), hydroxyethylcellulose (HEC), hydroxypropylcellulose (HPC), hydroxypropyl-methylcellulose (HPMC), and sodium carboxymethylcellulose (NaCMC), and other swellable hydrophilic polymers such as polyvinyl alcohol (PVA), hyaluronic acid or a salt thereof (e.g., sodium hyaluronate), and crosslinked acrylic acid polymers commonly referred to as "carbomers" (and available from B.F. Goodrich as Carbopol® polymers). The preferred amount of any thickener is such that a viscosity in the range of about 15 cps to 25 cps is provided, as a solution having a viscosity in the aforementioned range is generally considered optimal for both comfort and retention of the formulation in the eye. Any suitable isotonic agents and buffering agents commonly used in ophthalmic formulations may be used, providing that the osmotic pressure of the solution does not deviate from that of lachrymal fluid by more than 2-3% and that the pH of the formulation is maintained in the range of about 6.5 to about 8.0, preferably in the range of about 6.8 to about 7.8, and optimally at a pH of about 7.4. Preferred buffering agents include carbonates such as sodium and potassium bicarbonate.

Various tonicity agents are optionally employed to adjust the tonicity of the composition, preferably to that of natural tears for ophthalmic compositions. For example, sodium chloride, potassium chloride, magnesium chloride, calcium chloride, dextrose and/or mannitol are added to the composition to approximate physiological tonicity. Such an amount of tonicity agent will vary, depending on the particular agent to be added. In general, however, the compositions have a tonicity agent in an amount sufficient to cause the final composition to have an ophthalmically acceptable osmolality (generally about 150-450 mOsm, preferably 250-350 mOsm).

The pharmaceutically acceptable ophthalmic carrier used with the formulations of the invention may be of a wide range of types known to those of skill in the art. For example, the formulations of the invention are optionally provided as an ophthalmic solution or suspension, in which case the carrier is at least partially aqueous. Optionally, the formulations are ointments, in which case the pharmaceutically acceptable carrier comprises an ointment base. Preferred ointment bases herein have a melting or softening point close to body temperature, and any ointment bases commonly used in ophthalmic preparations are advantageously employed. Common ointment bases include petrolatum and mixtures of petrolatum and mineral oil.

The formulations of the invention are optionally prepared as a hydrogel, dispersion, or colloidal suspension. Hydrogels are formed by incorporation of a swellable, gel-forming polymer such as those set forth above as suitable thickening agents (i.e., MC, HEC, HPC, HPMC, NaCMC, PVA, or hyaluronic acid or a salt thereof, e.g., sodium hyaluronate), except that a formulation referred to in the art as a "hydrogel" typically has a higher viscosity than a formulation referred to as a "thickened" solution or suspension. In contrast to such preformed hydrogels, a formulation may also be prepared so as to form a hydrogel in situ following application to the eye. Such gels are liquid at room temperature but gel at higher temperatures (and thus are termed "thermoreversible" hydrogels), such as when placed in contact with body fluids. Biocompatible polymers that impart this property include acrylic acid polymers and copolymers, N-isopropylacrylamide derivatives, and ABA block copolymers of ethylene oxide and propylene oxide (conventionally referred to as "poloxamers" and available under the Pluronic® tradename from BASF-Wyandotte). The formulations can also be prepared in the form of a dispersion or colloidal suspension. Preferred dispersions are liposomal, in which case the formulation is enclosed within "liposomes," microscopic vesicles composed of alternating aqueous compartments and lipid bilayers. Colloidal suspensions are generally formed from microparticles, i.e., from microspheres, nanospheres, microcapsules, or nanocapsules, wherein microspheres and nanospheres are generally monolithic particles of a polymer matrix in which the formulation is trapped, adsorbed, or otherwise contained, while with microcapsules and nanocapsules, the formulation is actually encapsulated. The upper limit for the size for these microparticles is about 5 μm to about 10 μm.

The formulations are optionally incorporated into a sterile ocular insert that provides for controlled release of the formulation over an extended time period, generally in the range of about 12 hours to 60 days, and possibly up to 12 months or more, following implantation of the insert into the conjunctiva, sclera, or pars plana, or into the anterior segment or posterior segment of the eye. One type of ocular insert is an implant in the form of a monolithic polymer matrix that gradually releases the formulation to the eye through diffusion and/or matrix degradation. With such an insert, it is preferred that the polymer be completely soluble and or biodegradable (i.e., physically or enzymatically eroded in the eye) so that removal of the insert is unnecessary. These types of inserts are well known in the art, and are typically composed of a water-swellable, gel-forming polymer such as collagen, polyvinyl alcohol, or a cellulosic polymer. Another type of insert that is used to deliver the present formulation is a diffusional implant in which the formulation is contained in a central reservoir enclosed within a permeable polymer membrane that allows for gradual diffusion of the formulation out of the implant. Optionally, osmotic inserts are used, i.e., implants in which the formulation is released as a result of an increase in osmotic pressure within the implant following application to the eye and subsequent absorption of lachrymal fluid.

These ocular inserts are implanted into any region of the eye, including the sclera and the anterior and posterior segments. One such insert is composed of a controlled release implant containing a formulation that consists essentially of the active agent and a pharmaceutically acceptable carrier. The insert is a gradually but completely soluble implant, such as may be made by incorporating swellable, hydrogel-forming polymers into an aqueous liquid formulation. Alternatively, the insert is insoluble, in which case the agent is released from an internal reservoir through an outer membrane via diffusion or osmosis.

The term "controlled release" refers to an agent-containing formulation or fraction thereof in which release of the agent is not immediate, i.e., with a "controlled release" formulation, administration does not result in immediate release of the agent into an absorption pool. The term is used interchangeably with "nonimmediate release" as defined in Remington: The Science and Practice of Pharmacy, Nineteenth Ed. (Easton, Pa.: Mack Publishing Company, 1995). In general, the term "controlled release" as used herein refers to "sustained release" rather than to "delayed release" formulations. The term "sustained release" (synonymous with "extended release") is used in its conventional sense to refer to a formulation that provides for gradual release of an agent over an extended period of time.

In one aspect, an ophthalmic formulation of the invention is administered topically. Optionally, topical ophthalmic products are packaged in multidose form. Preservatives may thus be required to prevent microbial contamination during use. Suitable preservatives include: chlorobutanol, methyl paraben, propyl paraben, phenylethyl alcohol, edetate disodium, sorbic acid, polyquaternium-1, or other agents known to those skilled in the art. Such preservatives are typically employed at a level of from 0.001 to 1.0% w/v. Unit dose compositions of the present invention will be sterile, but typically unpreserved. Such compositions, therefore, generally will not contain preservatives. However, the ophthalmic compositions of the present invention are preferably preservative free and packaged in unit dose form.

The preferred compositions of the present invention are intended for administration to a mammal in need thereof, in particular to a human patient. In general, the doses used for the above described purposes will vary, but will be in an effective amount to eliminate or improve dry eye conditions. Generally, 1-2 drops of such compositions will be administered one or more times per day. For example, the composition can be administered 2 to 3 times a day or as directed by an eye care provider.

EXAMPLES

Example 1

Biomarkers for Proliferative Diabetic Retinopathy

Isolation of OIR-specific phage from a library containing in excess of $10^8$ phage was accomplished using a simple biopanning procedure in which the phage are allowed to interact with the surface of retinas prepared from rats that do (OIR) or do not (RA) have pathological retinal vessels. Following incubation of OIR retinas with the library, the retinas were washed extensively (to remove the un-bound phage) and the phage that associated with the surface of the OIR retina were eluted in 50 mM glycine pH 2.2. This population included a mixture of phage that recognized either the pathological neovessels or the other portion of the retina. Consequently, the abundance of phage that recognized the non-pathological structures was reduced by biopanning the population over 5 RA retinas. In this step, phage that did NOT bind to the retina were retained because the goal was to clear the population of phage that recognized healthy regions of a retina. Phage that remained at the end of this series of subtractions were termed OIR1-RA5. This population underwent 4 subsequent rounds of biopanning over OIR retinas, and the resulting populations were termed OIR2, OIR3, OIR4, OIR5.

Figure 2:
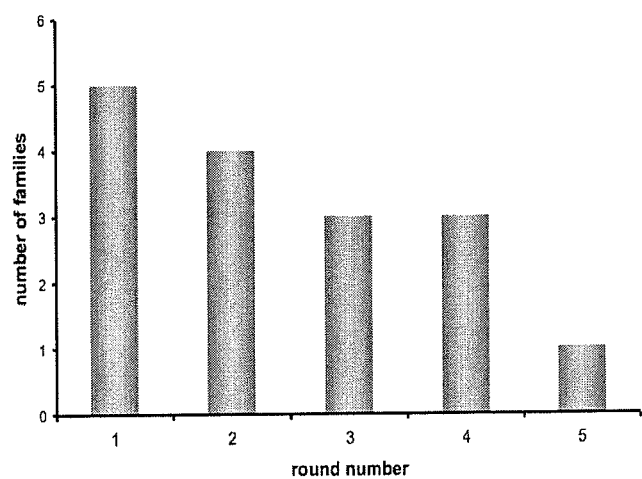
FIG. 2 is a bar graph demonstrating the decrease of phage family numbers, which indicates an increase in library homogeneity.

A measure of successful panning is an increase in library homogeneity, which was assessed by sequencing the DNA corresponding to the unique peptide insert of the phage. To this end, 30 phage from each of the 5 rounds were sequenced and the resulting data were analyzed using Lasergene 7.2 software, which identifies and groups the sequences into families. FIG. 1 shows the results from OIR3; there are 3 families (MT, RI, QI). FIG. 2 is a bar graph demonstrating the number of families as a function of the number of rounds of panning. The panning began with 5 families and ended with only one family. Thus, the expected increase in homogeneity was observed.

The phage with an insert encoding STEALRH (SH peptide; SEQ ID NO: 2) emerged early and ultimately was the only family remaining (FIG. 3), suggesting that such an insert is a very strong binder to an epitope on OIR retinas.

Example 2

SH Phage is Selective for Pathological Retinal Vessels

Figure 4:
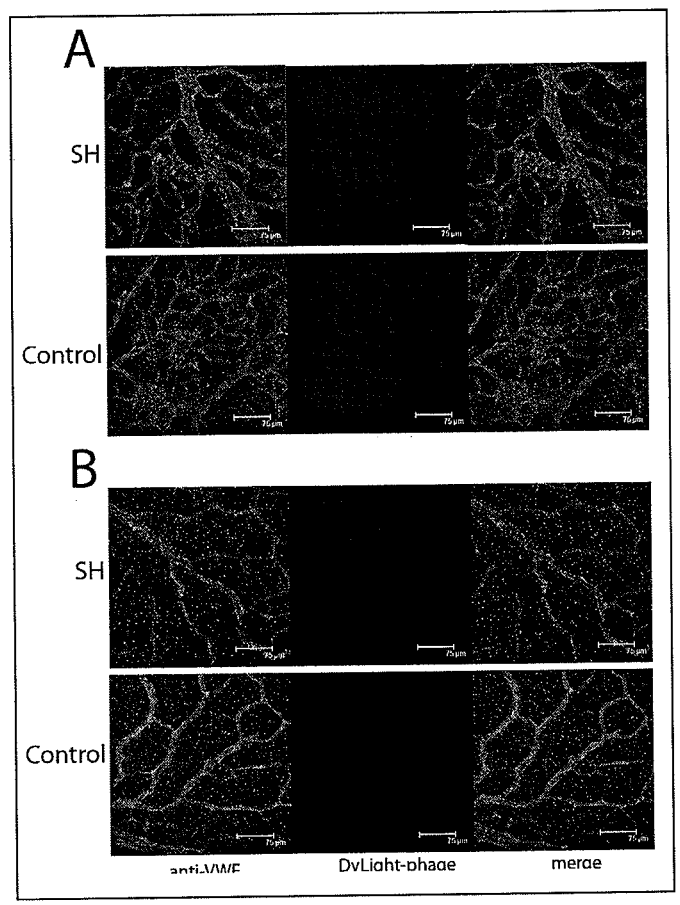
FIG. 4 is a series of photomicrographs that demonstrate that SH phage was selective for pathological retinal vessels.

The following experiments were performed to test if the phage selected in the biopanning procedure described above recognized the pathological regions of the OIR retinas. The phage was labeled with fluorescent dye DyLight 649 and incubated with retinas at a concentration of $5 \times 10^{11}$ pfu/retina. The retina was washed and examined by confocal microscopy. In parallel, the retinas were stained with an anti-vWF antibody in order to visualize the vasculature. In FIG. 4, the green color indicates vasculature, whereas the blue color is phage. In FIGS. 4A and 4B, the top row was stained with the SH phage, which has a unique peptide insert sequence (STEALRH; SEQ ID NO: 2), whereas the bottom row was stained with the control phage that lacks a peptide insert. As shown in FIG. 4A, the SH selected phage recognized pathological vessels within an OIR retina, whereas the control phage did not. This panel also shows that SH phage did not decorate the healthy vessels within the OIR retina, and thereby demonstrates its selectivity for the neovessels. FIG. 4B further addresses the selectivity of the SH phage for pathological vessels; the SH phage failed to stain the healthy vessels present in the retina isolated from a control animal, i.e., not subjected to the OIR procedure. These data show successful isolation of phage that are capable of distinguishing between pathological and physiological retinal vessels. This represents a major advance in the development of biomarkers for PDR.

Example 3

Characterization and Optimization of the Imaging Tools for Pathological Retinal Vessels To determine whether the unique peptide insert present in the SH phage is necessary and sufficient to recognize pathological retinal vessels, synthetic peptides corresponding to the unique peptide insert of the SH phage are examined for their ability to compete for the binding of the SH phage to pathological vessels. A scrambled version of the peptide is used in parallel to assess if the expected ability of the peptide to compete is dependent on its sequence. These experiments determine if the unique peptide insert is necessary for the SH phage to recognize pathological vessels.

The following series of experiments are performed to assess if the unique peptide insert of the SH phage is sufficient for recognition of pathological retinal vessels. A peptide corresponding to the unique insert and the 4 flanking residues on the N and 2 residues on the C termini (GGACSTEALRHCG; SEQ ID NO: 3) is synthesized. To facilitate labeling of the peptide biotin is added on the N-terminus, thereby allowing for detection of the peptide with the fluorescently labeled avidin. The labeled SH peptide, along with the scrambled version is labeled and used to stain flat mounts of RA (experienced room air instead of the OIR protocol) or OIR retinas as was done in FIG. 4. The staining protocol is optimized to identify the suitable concentration of peptide, incubation and wash conditions. If the peptides used in these experiments include all of the necessary sequence information to selectively recognize the pathological retinal vessels, then the peptides work comparably to the phage, as shown in FIG. 4.

Optionally, the number of amino acids flanking the unique peptide insert on C-terminus is increased from 2 to 7. In some cases, such larger peptides are designed with biotin attached on C-terminus instead N-terminus. If this strategy does not improve peptide binding, then portions of the SH phage substantially beyond the unique peptide insert are required for recognizing the pathological retinal vessels.

Additionally, human retinas are examined for whether the imaging tools developed using rat retinas recognize pathological vessels in humans. Pathological vessels are readily identified by examining the retinal vasculature (by staining flat mounts with anti-vWF as shown in FIG. 4).

The molecular determinant of pathological retinal vessels is determined. Identifying the binding partner for the SH phage provides insight into the pathogenesis of PDR. As shown in FIG. 4, the SH phage distinguishes between normal and pathological blood vessels. Thus, this phage recognizes something that is immediately surrounding these vessels and/or expressed on the surface of the endothelial cells of the neovasculature.

A particularly powerful approach to identifying the binding partner of the SH phage is to establish in vitro conditions that mimic those that induced the manifestation of the pathological vessels. To this end, monolayers of primary retinal endothelial cells are examined for their ability to become stainable with the SH phage when they are stimulated with a cocktail of pro-angiogenic factors, exposed to hypoxia, or cultured on different types of extracellular matrices. It is determined whether staining with SH phage becomes apparent with the cells, which are induced to organize into tubes in the presence or absence of pericytes. Provided that at least one of these changes promotes the staining of the SH phage, then the genes whose expression is regulated by such a change are profiled. To identify the best candidates for the SH phage binding partner within the resulting list those genes whose protein products are secreted or on the cell surface are examined. Subsequent biochemical studies are performed to evaluate the best candidates. These include direct interaction between the phage and the purified, recombinant protein, as well as increased and decreased binding of the SH phage to cells that over and under-express the candidate binding partner.

As mentioned above, the identity of the binding partner for the SH phage provides insight into the pathogenesis of PDR. For instance, if the SH phage is binding to an extracellular matrix protein that is liberated during pathological angiogenesis, then it would be determined if expression of the corresponding integrins on endothelial cells is also associated with manifestation of neovessels, and is interfering with the integrin/ECM interaction therapeutic.

The SH phage recognizes a non-endothelial cell type such as a macrophage or pericyte. This is examined by staining the retinal flat mounts with anti-bodies to detect such cells (anti-F4/80, -NG2, αSMA) instead of anti-vWF. Finally, it is determined if the SH phage recognizes a pre-clinical lesion by examining a series of retinas taken at time points prior to the manifestation of retinal neovascularization/tufts.

Example 4

SH Peptide Distinguishes Pathological from Healthy Retinas

Cellular Composition of Pathological Retinal Vessels

Figure 5:
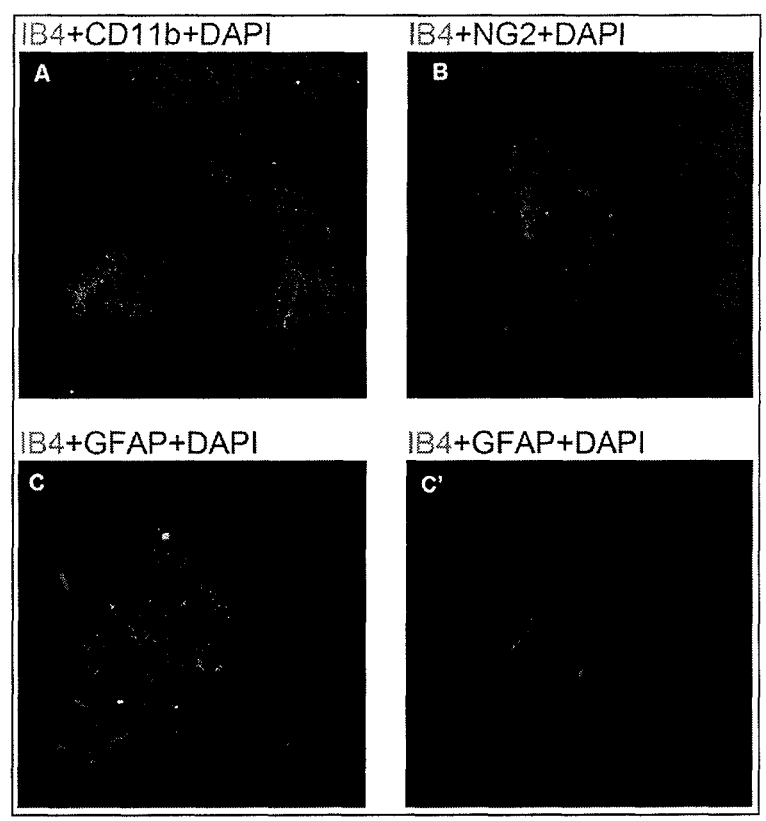
FIG. 5 is a series of confocal images of pathological vessels within an OIR retina stained with fluorescently labeled reagents diagnostic for various cell types. In all of the panels, the blue signal indicates 4',6-diamidino-2-phenylindole (DAPI) staining of the nuclei.

In the course of characterizing the pathology induced by the OIR (oxygen-induced retinopathy) procedure, the cellular composition of the pathological vasculature was observed. The neovessels of the OIR retina consisted of disorganized, 3-dimensional structures (tufts), located above the plane of the inner limiting membrane (ILM), extending into the retina and connecting to vessels of the superficial layer. In addition, there were sheets of abnormal vessels that formed ridges on the surface of the ILM. While both types of pathological neovessels were primarily composed of endothelial cells, they also contained the following cell types, listed in descending order of abundance: pericytes>macrophage/microglia≥activated astrocytes (FIG. 5). Both pericytes and macrophage/microglia were incorporated into the pathological vessels and juxtaposed to endothelial cells (ECs) (FIGS. 5A and B). The position of astrocytes was dependent on the location. At the surface of the ILM, astrocytes surrounded the tufts, but appeared physically separated from them (FIG. 5C). By contrast, astrocytes within the retina were integral to the neovessels (FIG. 5C'). Additional experiments indicated that phage recognizes only two of the 4 cell types present within the pathological neovessels: endothelial cells and macrophage/microglia.

Detection of Pathology that was Independent of Morphological Aberrations

Figure 6:
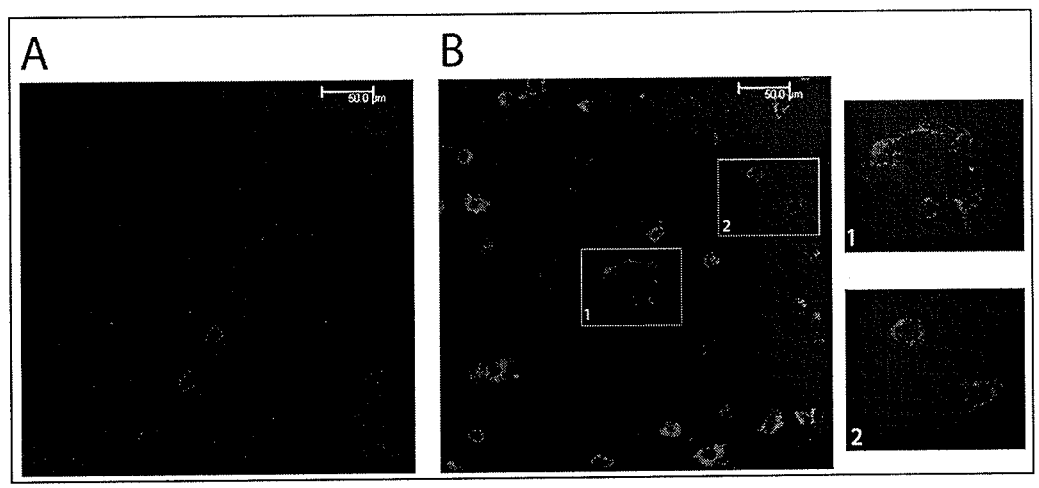
FIG. 6 is a series of confocal images of retina.

Pathological retinas (those that are isolated from rat pups subjected to the OIR procedure) contain abnormal vessels/tufts, which are associated with activated microglia/macrophages (FIG. 6B and enlargement #1). These activated cells were also present in areas that are devoid of vascular abnormalities (FIG. 6B and enlargement #2). The round shape of the CD11b-stained cells indicates that they are activated. More of these cells were observed in pathological retinas as compared with healthy retinas. FIG. 6 shows there are 20× more in the pathological retina.

Such activated cells were rare in a healthy retina (isolated from age-matched rat pups that were not subjected to the OIR procedure) (FIG. 6A). These findings indicate that morphologically obvious vascular irregularities may be an incomplete measure of ischemia-induced damage to the retinal vasculature.

SH Peptides Distinguished Pathological from Healthy Retinas

Figure 7:
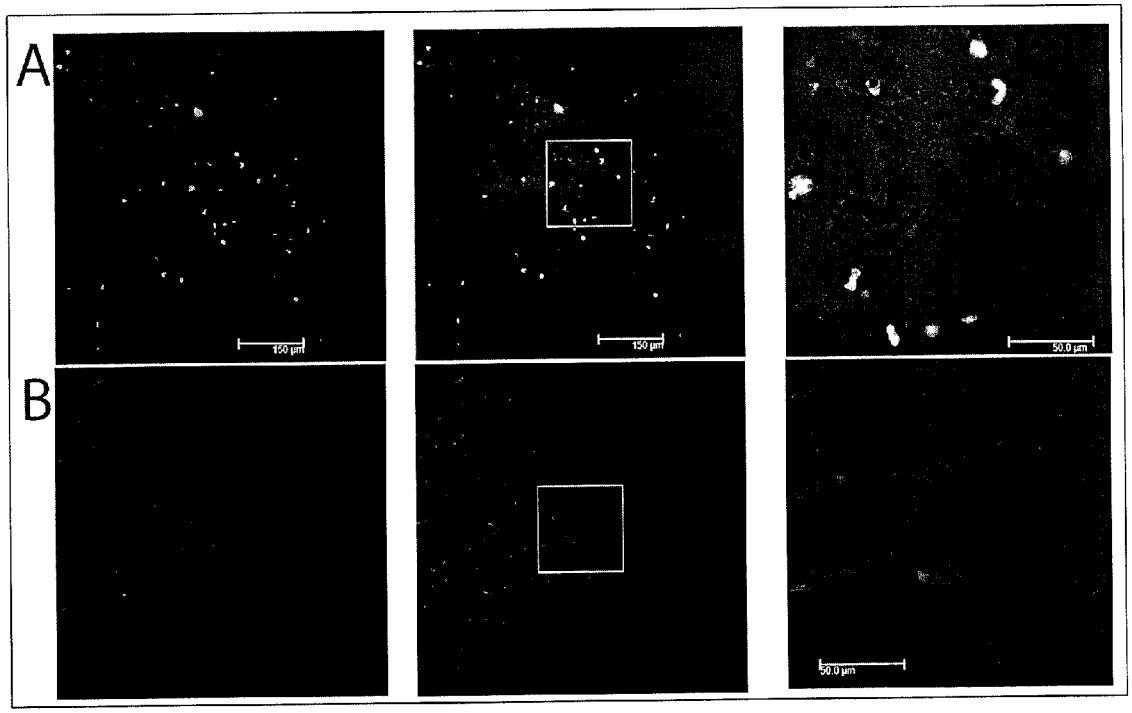
FIG. 7 is a series of confocal images of pathological (row A) and healthy (row B) retinas stained with either SH peptide alone (left hand column), the SH peptide and IB4, which decorates endothelial cells and activated macrophages/microglia (middle column), or SH peptide, IB4 and DAPI (right hand column). Yellow indicates either endothelial cells or activated macrophages/microglia that are also stained with the SH peptide. The first two columns are the same magnification (bars 150 mm), while the last column shows a magnified view of the areas that are boxed in the middle column.

Peptides corresponding to those expressed on the surface of the SH phage, e.g., those with the amino acid sequence STEALRH (SEQ ID NO: 2), recognized pathological retinas much more effectively than healthy retinas. As shown in FIG. 7, the SH peptide was superior to the entire SH phage in two ways: 1) strength of the signal, and 2) absence of background. The SH peptide consistently stained pathological retinas much more robustly than healthy retinas. In addition to staining tufts, the SH peptide recognized areas without overt pathology, and in this way is reminiscent of CD11b staining shown in FIGS. 5 and 6.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

---

What is claimed is:

1. A method of identifying retinal pathological neovascularization of a subject comprising locally administering to the retina of said subject a composition comprising a peptide consisting of the amino acid sequence of SEQ ID NO: 1, 2, or 3 that binds to pathological neovessels, and detecting binding of said peptide to retinal blood vessels of said subject, wherein said binding indicates retinal pathological neovascularization.

2. The method of claim 1, wherein said peptide is fluorescently labeled.

3. The method of claim 1, wherein said composition is in the form of eye drops, ointment, gel, or an ocular insert.

4. The method of claim 2, wherein said peptide is labeled with a fluorescent molecule selected from the group consisting of rhodamine, ethidium bromide, fluorescein, green fluorescent protein (GFP), or fluorescein isothiocyanate (FITC).

5. A method of treating retinal pathological neovascularization of an ophthalmic condition or disorder selected from retinopathy of prematurity, diabetic retinopathy, and age-related macular degeneration in a subject in need thereof comprising the steps of:
  (a) identifying a subject with the ophthalmic condition or disorder; and
  (b) locally administering to the retina of said subject a peptide consisting of the amino acid sequence of SEQ ID NO: 1, 2, or 3, linked to an anti-angiogenic agent selected from the group consisting of, angiopoietin-2, angiostatin, endostatin, tumstatin, pigment epithelium-derived factor, and a VEGF inhibitor, and a pharmaceutically acceptable carrier, thereby reducing pathological neovascularization.

6. The method of claim 5, wherein said peptide linked to said anti-angiogenic agent is in the form of eye drops, ointment, gel, or an ocular insert.

* * * * *

UNITED STATES PATENT AND TRADEMARK OFFICE
CERTIFICATE OF CORRECTION

PATENT NO.        : 8,722,015 B2
APPLICATION NO.   : 13/078331
DATED             : May 13, 2014
INVENTOR(S)       : Andrius Kazlauskas et al.

It is certified that error appears in the above-identified patent and that said Letters Patent is hereby corrected as shown below:

On the Title Page, under OTHER PUBLICATIONS, the eighth-listed author "Landenranta" should read --Lahdenranta--.

Signed and Sealed this
Second Day of September, 2014

Michelle K. Lee
*Deputy Director of the United States Patent and Trademark Office*

SEQUENCE LISTING

```
<160> NUMBER OF SEQ ID NOS: 66

<210> SEQ ID NO 1
<211> LENGTH: 9
<212> TYPE: PRT
<213> ORGANISM: Artificial Sequence
<220> FEATURE:
<223> OTHER INFORMATION: Protein from peptide library

<400> SEQUENCE: 1

Cys Ser Thr Glu Ala Leu Arg His Cys
```

```
<210> SEQ ID NO 2
<211> LENGTH: 7
<212> TYPE: PRT
<213> ORGANISM: Artificial Sequence
<220> FEATURE:
<223> OTHER INFORMATION: Protein from peptide library

<400> SEQUENCE: 2

Ser Thr Glu Ala Leu Arg His
1               5

<210> SEQ ID NO 3
<211> LENGTH: 13
<212> TYPE: PRT
<213> ORGANISM: Artificial Sequence
<220> FEATURE:
<223> OTHER INFORMATION: Chemically synthesized peptide

<400> SEQUENCE: 3

Gly Gly Ala Cys Ser Thr Glu Ala Leu Arg His Cys Gly
1               5                   10

<210> SEQ ID NO 4
<211> LENGTH: 7
<212> TYPE: PRT
<213> ORGANISM: Artificial Sequence
<220> FEATURE:
<223> OTHER INFORMATION: Protein from peptide library

<400> SEQUENCE: 4

His Ser Asn Tyr Asn Pro Arg
1               5

<210> SEQ ID NO 5
<211> LENGTH: 7
<212> TYPE: PRT
<213> ORGANISM: Artificial Sequence
<220> FEATURE:
<223> OTHER INFORMATION: Protein from peptide library

<400> SEQUENCE: 5

His Tyr His Glu Gln Leu Arg
1               5

<210> SEQ ID NO 6
<211> LENGTH: 7
<212> TYPE: PRT
<213> ORGANISM: Artificial Sequence
<220> FEATURE:
<223> OTHER INFORMATION: Protein from peptide library

<400> SEQUENCE: 6

Lys Ser Met Glu Ala Asp Thr
1               5

<210> SEQ ID NO 7
<211> LENGTH: 7
<212> TYPE: PRT
<213> ORGANISM: Artificial Sequence
<220> FEATURE:
<223> OTHER INFORMATION: Protein from peptide library

<400> SEQUENCE: 7

Gln Lys Gln Pro His Ser Val
1               5
```

```
<210> SEQ ID NO 8
<211> LENGTH: 7
<212> TYPE: PRT
<213> ORGANISM: Artificial Sequence
<220> FEATURE:
<223> OTHER INFORMATION: Protein from peptide library

<400> SEQUENCE: 8

Gln Lys Gln Asp Ser Thr Trp
1               5

<210> SEQ ID NO 9
<211> LENGTH: 7
<212> TYPE: PRT
<213> ORGANISM: Artificial Sequence
<220> FEATURE:
<223> OTHER INFORMATION: Protein from peptide library

<400> SEQUENCE: 9

Gln Thr Met Leu Ser Leu Asn
1               5

<210> SEQ ID NO 10
<211> LENGTH: 7
<212> TYPE: PRT
<213> ORGANISM: Artificial Sequence
<220> FEATURE:
<223> OTHER INFORMATION: Protein from peptide library

<400> SEQUENCE: 10

Pro Ala Gln Leu Leu Asn Ala
1               5

<210> SEQ ID NO 11
<211> LENGTH: 7
<212> TYPE: PRT
<213> ORGANISM: Artificial Sequence
<220> FEATURE:
<223> OTHER INFORMATION: Protein from peptide library

<400> SEQUENCE: 11

Thr Val Asp Lys Pro Pro Gly
1               5

<210> SEQ ID NO 12
<211> LENGTH: 7
<212> TYPE: PRT
<213> ORGANISM: Artificial Sequence
<220> FEATURE:
<223> OTHER INFORMATION: Protein from peptide library

<400> SEQUENCE: 12

Gln Pro Pro Phe Pro Arg Pro
1               5

<210> SEQ ID NO 13
<211> LENGTH: 7
<212> TYPE: PRT
<213> ORGANISM: Artificial Sequence
<220> FEATURE:
<223> OTHER INFORMATION: Protein from peptide library

<400> SEQUENCE: 13

Arg Phe Asn Thr Pro Leu Pro
1               5

<210> SEQ ID NO 14
```

```
<211> LENGTH: 7
<212> TYPE: PRT
<213> ORGANISM: Artificial Sequence
<220> FEATURE:
<223> OTHER INFORMATION: Protein from peptide library

<400> SEQUENCE: 14

Arg His Ser Ala Asn Gln Thr
1               5

<210> SEQ ID NO 15
<211> LENGTH: 7
<212> TYPE: PRT
<213> ORGANISM: Artificial Sequence
<220> FEATURE:
<223> OTHER INFORMATION: Protein from peptide library

<400> SEQUENCE: 15

Tyr Gln Asp Pro Arg Gln Pro
1               5

<210> SEQ ID NO 16
<211> LENGTH: 7
<212> TYPE: PRT
<213> ORGANISM: Artificial Sequence
<220> FEATURE:
<223> OTHER INFORMATION: Protein from peptide library

<400> SEQUENCE: 16

Glu Gly Leu Ser Glu Ile Glu
1               5

<210> SEQ ID NO 17
<211> LENGTH: 7
<212> TYPE: PRT
<213> ORGANISM: Artificial Sequence
<220> FEATURE:
<223> OTHER INFORMATION: Protein from peptide sequence

<400> SEQUENCE: 17

Pro Gln Leu Ser Asp Ala Gly
1               5

<210> SEQ ID NO 18
<211> LENGTH: 7
<212> TYPE: PRT
<213> ORGANISM: Artificial Sequence
<220> FEATURE:
<223> OTHER INFORMATION: Protein from peptide library

<400> SEQUENCE: 18

Leu Pro Leu Arg Ser Ile Gln
1               5

<210> SEQ ID NO 19
<211> LENGTH: 7
<212> TYPE: PRT
<213> ORGANISM: Artificial Sequence
<220> FEATURE:
<223> OTHER INFORMATION: Protein from peptide library

<400> SEQUENCE: 19

Leu Pro Asn Ile Asp Ala Lys
1               5

<210> SEQ ID NO 20
<211> LENGTH: 7
<212> TYPE: PRT
```

```
<213> ORGANISM: Artificial Sequence
<220> FEATURE:
<223> OTHER INFORMATION: Protein from peptide library

<400> SEQUENCE: 20

Pro Asn Ser Arg Val Ala Ala
1               5

<210> SEQ ID NO 21
<211> LENGTH: 7
<212> TYPE: PRT
<213> ORGANISM: Artificial Sequence
<220> FEATURE:
<223> OTHER INFORMATION: Protein from peptide library

<400> SEQUENCE: 21

Arg Pro Ser His Ala Thr Pro
1               5

<210> SEQ ID NO 22
<211> LENGTH: 7
<212> TYPE: PRT
<213> ORGANISM: Artificial Sequence
<220> FEATURE:
<223> OTHER INFORMATION: Protein from peptide library

<400> SEQUENCE: 22

Ser Ala Gly Phe Thr Trp Leu
1               5

<210> SEQ ID NO 23
<211> LENGTH: 7
<212> TYPE: PRT
<213> ORGANISM: Artificial Sequence
<220> FEATURE:
<223> OTHER INFORMATION: Protein from peptide library

<400> SEQUENCE: 23

Ser Leu Glu Met Thr Trp Lys
1               5

<210> SEQ ID NO 24
<211> LENGTH: 7
<212> TYPE: PRT
<213> ORGANISM: Artificial Sequence
<220> FEATURE:
<223> OTHER INFORMATION: Protein from peptide library

<400> SEQUENCE: 24

Arg Ser Pro Met Thr Thr Tyr
1               5

<210> SEQ ID NO 25
<211> LENGTH: 7
<212> TYPE: PRT
<213> ORGANISM: Artificial Sequence
<220> FEATURE:
<223> OTHER INFORMATION: Protein from peptide library

<400> SEQUENCE: 25

Ile Glu Ser Pro Thr Tyr Trp
1               5

<210> SEQ ID NO 26
<211> LENGTH: 7
<212> TYPE: PRT
<213> ORGANISM: Artificial Sequence
<220> FEATURE:
```

```
<223> OTHER INFORMATION: Protein from peptide library

<400> SEQUENCE: 26

His Gln Ser Ser Pro Lys Leu
1               5

<210> SEQ ID NO 27
<211> LENGTH: 7
<212> TYPE: PRT
<213> ORGANISM: Artificial Sequence
<220> FEATURE:
<223> OTHER INFORMATION: Protein from peptide library

<400> SEQUENCE: 27

Gln Ser Ser Pro Pro Ser Leu
1               5

<210> SEQ ID NO 28
<211> LENGTH: 7
<212> TYPE: PRT
<213> ORGANISM: Artificial Sequence
<220> FEATURE:
<223> OTHER INFORMATION: Protein from peptide library

<400> SEQUENCE: 28

Leu Ile Thr Pro Ser Arg Leu
1               5

<210> SEQ ID NO 29
<211> LENGTH: 7
<212> TYPE: PRT
<213> ORGANISM: Artificial Sequence
<220> FEATURE:
<223> OTHER INFORMATION: Protein from peptide library

<400> SEQUENCE: 29

Asn Pro Asp Arg Tyr Tyr Thr
1               5

<210> SEQ ID NO 30
<211> LENGTH: 7
<212> TYPE: PRT
<213> ORGANISM: Artificial Sequence
<220> FEATURE:
<223> OTHER INFORMATION: Protein from peptide library

<400> SEQUENCE: 30

Asn Ser Thr His Lys Met Phe
1               5

<210> SEQ ID NO 31
<211> LENGTH: 7
<212> TYPE: PRT
<213> ORGANISM: Artificial Sequence
<220> FEATURE:
<223> OTHER INFORMATION: Protein from peptide library

<400> SEQUENCE: 31

Tyr Leu Gln Leu Leu Leu Thr
1               5

<210> SEQ ID NO 32
<211> LENGTH: 7
<212> TYPE: PRT
<213> ORGANISM: Artificial Sequence
<220> FEATURE:
<223> OTHER INFORMATION: Protein from peptide library
```

```
<400> SEQUENCE: 32

Pro Gly Arg Gln Ala Met Pro
1               5

<210> SEQ ID NO 33
<211> LENGTH: 7
<212> TYPE: PRT
<213> ORGANISM: Artificial Sequence
<220> FEATURE:
<223> OTHER INFORMATION: Protein from peptide library

<400> SEQUENCE: 33

Thr Pro Ile Thr Leu Ser Thr
1               5

<210> SEQ ID NO 34
<211> LENGTH: 7
<212> TYPE: PRT
<213> ORGANISM: Artificial Sequence
<220> FEATURE:
<223> OTHER INFORMATION: Protein from peptide library

<400> SEQUENCE: 34

Arg Ala Tyr Gln Leu Gln Gln
1               5

<210> SEQ ID NO 35
<211> LENGTH: 7
<212> TYPE: PRT
<213> ORGANISM: Artificial Sequence
<220> FEATURE:
<223> OTHER INFORMATION: Protein from peptide library

<400> SEQUENCE: 35

Ser His Glu Ala Leu Arg His
1               5

<210> SEQ ID NO 36
<211> LENGTH: 7
<212> TYPE: PRT
<213> ORGANISM: Artificial Sequence
<220> FEATURE:
<223> OTHER INFORMATION: Protein  from peptide library

<400> SEQUENCE: 36

Ser Ser Glu Ala Tyr Arg His
1               5

<210> SEQ ID NO 37
<211> LENGTH: 7
<212> TYPE: PRT
<213> ORGANISM: Artificial Sequence
<220> FEATURE:
<223> OTHER INFORMATION: Protein from peptide library

<400> SEQUENCE: 37

Asn Met Asp Thr Ala Arg Leu
1               5

<210> SEQ ID NO 38
<211> LENGTH: 7
<212> TYPE: PRT
<213> ORGANISM: Artificial Sequence
<220> FEATURE:
<223> OTHER INFORMATION: Protein from peptide library

<400> SEQUENCE: 38
```

```
Ser Thr Thr Pro Ser Arg Met
1               5

<210> SEQ ID NO 39
<211> LENGTH: 7
<212> TYPE: PRT
<213> ORGANISM: Artificial Sequence
<220> FEATURE:
<223> OTHER INFORMATION: Protein from peptide sequence

<400> SEQUENCE: 39

Asp Ser Thr Thr Pro Arg Ser
1               5

<210> SEQ ID NO 40
<211> LENGTH: 7
<212> TYPE: PRT
<213> ORGANISM: Artificial Sequence
<220> FEATURE:
<223> OTHER INFORMATION: Protein from peptide library

<400> SEQUENCE: 40

Ser Gln Pro Thr Leu Gln Ala
1               5

<210> SEQ ID NO 41
<211> LENGTH: 7
<212> TYPE: PRT
<213> ORGANISM: Artificial Sequence
<220> FEATURE:
<223> OTHER INFORMATION: Protein from peptide library

<400> SEQUENCE: 41

Thr Pro Thr Thr Ser Pro Ala
1               5

<210> SEQ ID NO 42
<211> LENGTH: 7
<212> TYPE: PRT
<213> ORGANISM: Artificial Sequence
<220> FEATURE:
<223> OTHER INFORMATION: Protein from peptide library

<400> SEQUENCE: 42

Met His Ser Gly Pro Met Ala
1               5

<210> SEQ ID NO 43
<211> LENGTH: 7
<212> TYPE: PRT
<213> ORGANISM: Artificial Sequence
<220> FEATURE:
<223> OTHER INFORMATION: Protein from peptide library

<400> SEQUENCE: 43

Ala Asn Leu His His Gln Gln
1               5

<210> SEQ ID NO 44
<211> LENGTH: 7
<212> TYPE: PRT
<213> ORGANISM: Artificial Sequence
<220> FEATURE:
<223> OTHER INFORMATION: Protein from peptide library

<400> SEQUENCE: 44

Ser Glu Tyr Leu Trp Ser Thr
1               5
```

```
<210> SEQ ID NO 45
<211> LENGTH: 7
<212> TYPE: PRT
<213> ORGANISM: Artificial Sequence
<220> FEATURE:
<223> OTHER INFORMATION: Protein from peptide library

<400> SEQUENCE: 45

Asn Phe Thr Trp Thr Ser Leu
1               5

<210> SEQ ID NO 46
<211> LENGTH: 7
<212> TYPE: PRT
<213> ORGANISM: Artificial Sequence
<220> FEATURE:
<223> OTHER INFORMATION: Protein from peptide library

<400> SEQUENCE: 46

Asn Lys Leu Glu Pro Phe Arg
1               5

<210> SEQ ID NO 47
<211> LENGTH: 7
<212> TYPE: PRT
<213> ORGANISM: Artificial Sequence
<220> FEATURE:
<223> OTHER INFORMATION: Protein from peptide library

<400> SEQUENCE: 47

Tyr Pro Thr His Pro Tyr Ser
1               5

<210> SEQ ID NO 48
<211> LENGTH: 7
<212> TYPE: PRT
<213> ORGANISM: Artificial Sequence
<220> FEATURE:
<223> OTHER INFORMATION: Protein from peptide library

<400> SEQUENCE: 48

Lys Trp Ser Pro Pro Gln Ser
1               5

<210> SEQ ID NO 49
<211> LENGTH: 7
<212> TYPE: PRT
<213> ORGANISM: Artificial Sequence
<220> FEATURE:
<223> OTHER INFORMATION: Protein from peptide library

<400> SEQUENCE: 49

Met Ser Pro Lys Asn Val Ser
1               5

<210> SEQ ID NO 50
<211> LENGTH: 7
<212> TYPE: PRT
<213> ORGANISM: Artificial Sequence
<220> FEATURE:
<223> OTHER INFORMATION: Protein from peptide library

<400> SEQUENCE: 50

Pro Thr Ala Lys Ser Ala Ser
1               5
```

```
<210> SEQ ID NO 51
<211> LENGTH: 7
<212> TYPE: PRT
<213> ORGANISM: Artificial Sequence
<220> FEATURE:
<223> OTHER INFORMATION: Protein from peptide library

<400> SEQUENCE: 51

Leu Ala Pro Thr Ala Asn Ser
1               5

<210> SEQ ID NO 52
<211> LENGTH: 7
<212> TYPE: PRT
<213> ORGANISM: Artificial Sequence
<220> FEATURE:
<223> OTHER INFORMATION: Protein from peptide library

<400> SEQUENCE: 52

Asn Gln Lys Thr Thr Ser Ser
1               5

<210> SEQ ID NO 53
<211> LENGTH: 7
<212> TYPE: PRT
<213> ORGANISM: Artificial Sequence
<220> FEATURE:
<223> OTHER INFORMATION: Protein from peptide library

<400> SEQUENCE: 53

Val Asp Lys Ser Phe Asn Ile
1               5

<210> SEQ ID NO 54
<211> LENGTH: 7
<212> TYPE: PRT
<213> ORGANISM: Artificial Sequence
<220> FEATURE:
<223> OTHER INFORMATION: Protein from peptide library

<400> SEQUENCE: 54

Gly Leu Asn Val Met Arg Tyr
1               5

<210> SEQ ID NO 55
<211> LENGTH: 7
<212> TYPE: PRT
<213> ORGANISM: Artificial Sequence
<220> FEATURE:
<223> OTHER INFORMATION: Protein from peptide library

<400> SEQUENCE: 55

Pro Asp Asn Lys Leu Arg Gln
1               5

<210> SEQ ID NO 56
<211> LENGTH: 7
<212> TYPE: PRT
<213> ORGANISM: Artificial Sequence
<220> FEATURE:
<223> OTHER INFORMATION: Protein from peptide library

<400> SEQUENCE: 56

Asp Gly Gln Ser Thr Leu Arg
1               5

<210> SEQ ID NO 57
<211> LENGTH: 7
```

```
<212> TYPE: PRT
<213> ORGANISM: Artificial Sequence
<220> FEATURE:
<223> OTHER INFORMATION: Protein from peptide library

<400> SEQUENCE: 57

His Asp Asn Arg Ser Ala Leu
1               5

<210> SEQ ID NO 58
<211> LENGTH: 7
<212> TYPE: PRT
<213> ORGANISM: Artificial Sequence
<220> FEATURE:
<223> OTHER INFORMATION: Protein from peptide library

<400> SEQUENCE: 58

Glu Gln Pro Tyr Ser Ser Ile
1               5

<210> SEQ ID NO 59
<211> LENGTH: 7
<212> TYPE: PRT
<213> ORGANISM: Artificial Sequence
<220> FEATURE:
<223> OTHER INFORMATION: Protein from peptide library

<400> SEQUENCE: 59

Arg Asp Met Gly Asn His Ile
1               5

<210> SEQ ID NO 60
<211> LENGTH: 7
<212> TYPE: PRT
<213> ORGANISM: Artificial Sequence
<220> FEATURE:
<223> OTHER INFORMATION: Protein from peptide library

<400> SEQUENCE: 60

Asn Ser Tyr Thr Asn Ala Ala
1               5

<210> SEQ ID NO 61
<211> LENGTH: 7
<212> TYPE: PRT
<213> ORGANISM: Artificial Sequence
<220> FEATURE:
<223> OTHER INFORMATION: Protein from peptide library

<400> SEQUENCE: 61

Asp Thr Thr Asn Ser His Leu
1               5

<210> SEQ ID NO 62
<211> LENGTH: 7
<212> TYPE: PRT
<213> ORGANISM: Artificial Sequence
<220> FEATURE:
<223> OTHER INFORMATION: Protein from peptide library

<400> SEQUENCE: 62

Gln Gln Pro Thr Ser Gly His
1               5

<210> SEQ ID NO 63
<211> LENGTH: 7
<212> TYPE: PRT
<213> ORGANISM: Artificial Sequence
```

```
<220> FEATURE:
<223> OTHER INFORMATION: Protein from peptide library

<400> SEQUENCE: 63

Thr Glu Arg Gln Thr Arg Phe
1               5

<210> SEQ ID NO 64
<211> LENGTH: 7
<212> TYPE: PRT
<213> ORGANISM: Artificial Sequence
<220> FEATURE:
<223> OTHER INFORMATION: Protein from peptide library

<400> SEQUENCE: 64

Lys Thr Pro Phe Gln His Thr
1               5

<210> SEQ ID NO 65
<211> LENGTH: 7
<212> TYPE: PRT
<213> ORGANISM: Artificial Sequence
<220> FEATURE:
<223> OTHER INFORMATION: Protein from peptide library

<400> SEQUENCE: 65

Leu Gln Met Thr Lys Asn Ser
1               5

<210> SEQ ID NO 66
<211> LENGTH: 7
<212> TYPE: PRT
<213> ORGANISM: Artificial Sequence
<220> FEATURE:
<223> OTHER INFORMATION: Protein from peptide library

<400> SEQUENCE: 66

Asn Thr Glu Ala Leu Arg His
1               5
```